US006329559B1

(12) United States Patent
Sievert et al.

(10) Patent No.: US 6,329,559 B1
(45) Date of Patent: Dec. 11, 2001

(54) PROCESSES FOR THE PRODUCTION OF HEXAFLUOROPROPENE AND OPTIONALLY OTHER HALOGENATED HYDROCARBONS CONTAINING FLUORINE

(75) Inventors: Allen Capron Sievert, Elkton, MD (US); V. N. Mallikarjuna Rao, Wilmington; Francis J. Walczak, New Castle, both of DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/701,448

(22) PCT Filed: Jun. 2, 1999

(86) PCT No.: PCT/US99/12246

§ 371 Date: Nov. 27, 2000

§ 102(e) Date: Nov. 27, 2000

(87) PCT Pub. No.: WO99/62851

PCT Pub. Date: Dec. 9, 1999

Related U.S. Application Data
(60) Provisional application No. 60/087,751, filed on Jun. 2, 1998.

(51) Int. Cl.$^7$ .................................................. C07C 17/08
(52) U.S. Cl. .......................... 570/165; 570/164; 570/166; 570/167; 570/168; 570/169
(58) Field of Search ..................... 570/165, 164, 570/166, 167, 168, 169

(56) References Cited

U.S. PATENT DOCUMENTS

| 2,576,823 | 11/1951 | Benning . |
|---|---|---|
| 5,043,491 | 8/1991 | Webster et al. . |
| 5,057,634 | 10/1991 | Webster et al. . |
| 5,068,472 | 11/1991 | Webster et al. . |
| 5,523,501 | 4/1996 | Kellner et al. . |
| 5,573,654 | 11/1996 | Cheurkov et al. . |

FOREIGN PATENT DOCUMENTS

| 1237084 | 3/1967 | (DE) . |
|---|---|---|
| 002098 | 5/1979 | (EP) . |
| 0 434 409 A | 6/1991 | (EP) . |
| 434 407A | 6/1991 | (EP) . |
| 821 211A | 10/1959 | (GB) . |
| 902590 | 8/1962 | (GB) . |
| 938 070 A | 9/1963 | (GB) . |
| 2 313 118 A | 11/1997 | (GB) . |
| WO 90 08748 A | 8/1990 | (WO) . |
| WO 91 05752 A | 5/1991 | (WO) . |
| WO 99/62849 | 12/1999 | (WO) . |

OTHER PUBLICATIONS

U.S. application No. 09/701,449, Sievert et al., see IDS.
J. Kricala et al., J. Fluorine, 43 (1989), pp. 155–175.

*Primary Examiner*—Alan Siegel

(57) ABSTRACT

A process is disclosed for the manufacture of $CF_3CF=CF_2$, and optionally a least one compound selected from $CF_3CH_2CF_3$ and $CF_3CHFCHF_2$. The process involves contacting a reactor feed including a precursor stream of at least one halogenated propane of the formula $CX_3CH_2CH_yX_{(3-y)}$ and/or halogenated propene of the formula $CX_3CH=CH_yX_{(2-y)}$, where each X is Cl or F and y is 0, 1 or 2 (provided that the average fluorine content of the precursor stream is no more than 5 fluorine substituents per molecule) with HF and $Cl_2$ in a chlorofluorination reaction zone containing a fluorination catalyst and operating at a temperature between about 150° C. and 400° C., to produce a reaction zone effluent including HF, HCl and a mixture of reaction products of the precursor feed which contains at least one compound of the formula $C_3Cl_2F_6$ including $CClF_2CClFCF_3$ and at least one compound of the formula $C_3HClF_6$, including $CHF_2CClFCF_3$ and has an average fluorine content which is at least one fluorine substituent per molecule more than the average fluorine content of the precursor stream. The chlorofluorination reaction zone effluent is distilled to produce (i) a low-boiling component including HCl (and when they are present in the reaction zone effluent, $C_3F_8$, $C_3ClF_7$ and $C_3HF_7$), (ii) a hydrogenation feed component containing at least one compo of the formula $C_3Cl_2F_6$ including $CClF_2CClFCF_3$ and at least one compound of the formnula $C_3HClF_6$ including $CHF_2CClFCF_3$, and an underfluorinated component including halogenated propanes containing at least one chlorine subtituent and from one to five fluorine substituents. The $CClF_2CClFCF_3$ and $CHF_2CClFCF_3$ of hydrogenation feed component (ii) is reacted with hydrogen to produce a mixture including $CF_3CF=CF_2$ and $CF_3CHFCHF_2$ and the $CF_3CF=CF_2$ from this product mixture is recovered. Underfluorinated component (iii) is returned to the chlorofluorination reaction zone.

20 Claims, 1 Drawing Sheet

PROCESSES FOR THE PRODUCTION OF HEXAFLUOROPROPENE AND OPTIONALLY OTHER HALOGENATED HYDROCARBONS CONTAINING FLUORINE

This application is a national filing under 35 USC 371 of International Application No. PCT/US99/12246 filed Jun. 2, 1999, claiming priority of U.S. Provisional Application No. 60/087,751 filed Jun. 2, 1998.

FIELD OF THE INVENTION

The present invention relates to the synthesis of hexafluoropropene, and optionally other halogenated hydrocarbons containing fluorine, especially 1,1,1,3,3,3-hexafluoropropane. and 1,1,1,2,3,3-hexafluoropropane.

BACKGROUND

Commercial methods for the preparation of hexafluoropropene ($CF_3CF=CF_2$ or HFP), a fluoromonomer, typically involve temperatures greater than 600° C. The high reaction temperatures lead to the formation of perfluoroisobutylene, an extremely toxic compound which is costly to remove and destroy (e.a., see European Patent Application No. 002,098). Processes for the manufacture of HFP at lower temperatures based on the use of acyclic three-carbon hydrocarbons or partially halogenated three-carbon hydrocarbons are disclosed in U.S. Pat. Nos. 5,043,491, 5,057,634 and 5,068,472.

1,1,1,2,3,3,3-Heptafluoropropane ($CF_3CHFCF_3$ or HFC-227ea), a fire extinguishant, can be prepared by the reaction of HF with HFP in contact with activated carbon (e.g., see British Patent Specification No. GB 902,590). The manufacture of HFC-227ea in this instance is tied to the availability HFP.

U.S. Pat. No. 5.573.654 reports the preparation of 1,1,1,3,3,3-hexafluoropropane ($CF_3CH_2CF_3$ or HFC-236fa), a fire extinguishant and refrigerant. by the reaction of extremely toxic perfluoroisobutylene with triethylamine and water. 1,1,1,2,3,3-Hexafluoropropane ($CF_3CHFCHF_2$ or HFC-236ea) is also a refrigerant.

There is a need for alternative methods of manufacturing HFP and other halogenated hydrocarbons containing fluorine. such as the fluorinated propanes HFC-236fa and HFC-236ea.

SUMMARY OF THE INVENTION

This invention provides a process for the manufacture of $CF_3CF=CF_2$, and optionally at least one compound selected from $CF_3CH_2CF_3$ and $CF_3CHFCHF_2$. The process comprises (a) contacting a reactor feed comprising a precursor stream of at least one compound selected from halogenated propanes of the formula $CX_3CH_2CH_yX_{(3-y)}$ and halogenated propenes of the formula $CX_3CH=CH_yX_{(2-y)}$, where each X is independently selected from Cl and F and y is 0, 1 or 2, provided that the average fluorine content of said precursor stream is no more than 5 fluorine substituents per molecule, with HF and $Cl_2$ in a chlorofluorination reaction zone containing a fluorination catalyst and operating at a temperature between about 150° C. and 400° C. to produce a reaction zone effluent comprising HF, HCl and a mixture of reaction products of said precursor stream which contains at least one compound of the formula $C_3Cl_2F_6$ including $CClF_2CClFCF_3$ and at least one compound of the formula $C_3HClF_6$ including $CHF_2CClFCF_3$ and has an average fluorine content which is at least one fluorine substituent per molecule more than the average fluorine content of the precursor stream, (b) distilling the reaction zone effluent of (a) to produce (i) a low-boiling component comprising HCl and when they are present in said reaction zone effluent, $C_3F_8$, $C_3ClF_7$ and $C_3HF_7$, (ii) a hydrogenation feed component comprising at least one compound of the formula $C_3Cl_2F_6$ including $CClF_2CClFCF_3$ and at least one compound of the formula $C_3HClF_6$ including $CHF_2CClFCF_3$, and (iii) an underfluorinated component comprising halogenated propanes containing at least one chlorine substituent and from one to five fluorine substituents; (c) reacting the $CClF_2CClFCF_3$ and $CHF_2CClFCF_3$ of hydrogenation feed component (ii) with hydrogen to produce a mixture comprising $CF_3CF=CF_2$ and $CF_3CHFCHF_2$; (d) recovering the $CF_3CF=CF$. from the product mixture of (c); and (e) returning the underfluorinated component (iii) to the chlorofluorination reaction zone.

DETAILED DESCRIPTION

Figure 1:
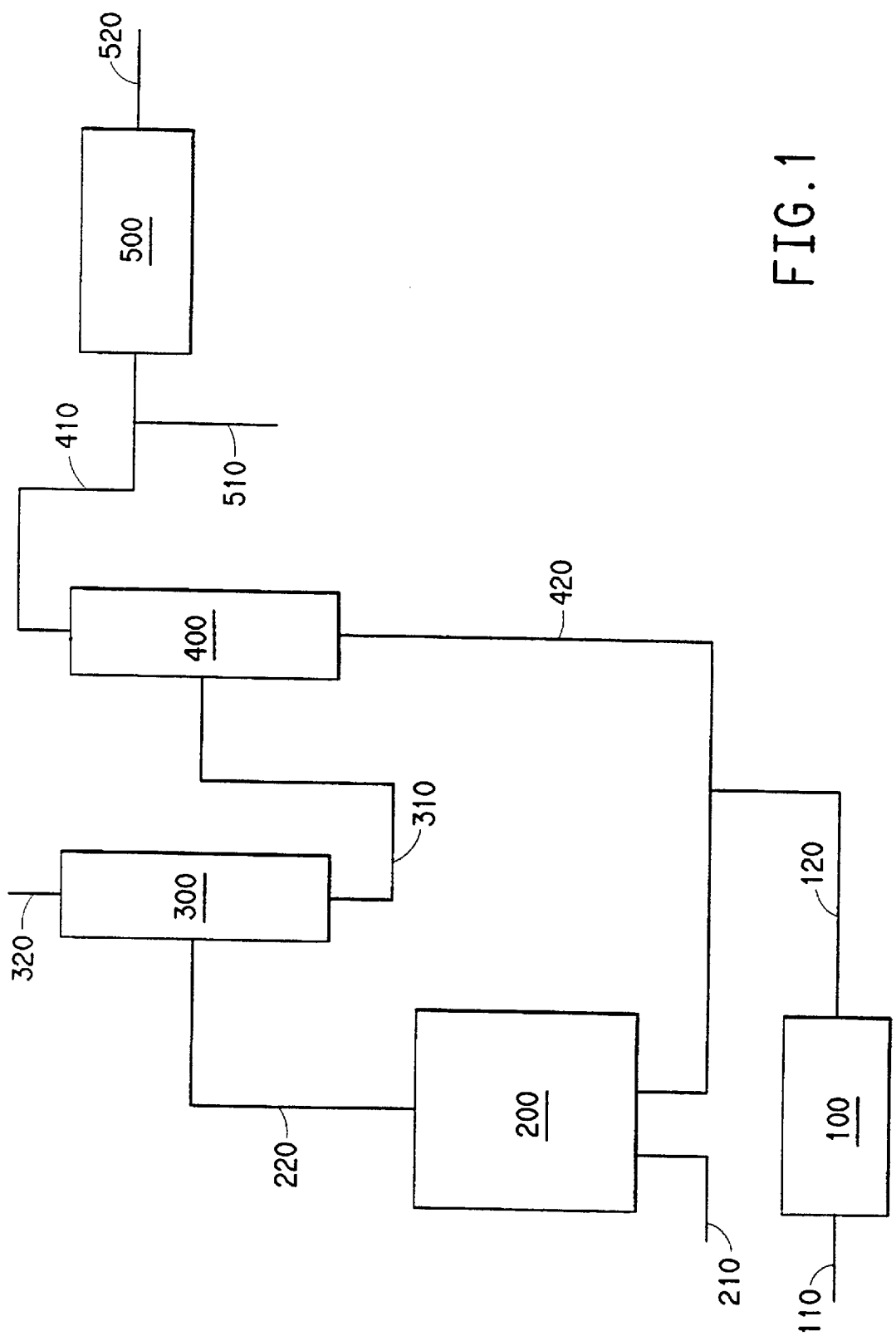
FIG. 1 is a schematic flow diagram of an embodiment of the process of this invention.

The present invention provides a multi step process for the preparation of 1,1,1,2,3,3-hexafluoropropene, optionally together with 1,1,1,3,3,3-hexafluoropropane, 1,1,1,2,3,3-hexafluoropropane, or mixtures thereof from readily available starting materials.

Suitable precursor stream compounds include the hydrochlorocarbons $CCl_3CH_2CH_2Cl$, $CCl_3CH_2CHCl_2$ and $CCl_3CH_2CCl_3$. However, in certain embodiments of this invention. the precursor stream compounds of (a) (i.e., halogenated propanes of the formula $CX_3CH_2CH_yX_{(3-y)}$ and halogenated propenes of the formula $CX_3CH=CH_yX_{(2-y)}$) can be prepared by reacting one or more of these hydrochlorocarbons (i.e., compounds of the formula $CCl_3CH_2CClZ_2$, where Z is independently selected from the group consisting of H and Cl) with substantially anhydrous HF in a reaction zone at a temperature of at least 80° C. but not more than about 250° C., to produce a reactor effluent comprising HF, HCl, $CF_3CH=CZ_2$, and $CF_3CH_2CZ_2F$ where Z is as defined above. Suitable hydrochlorocarbons reactants for this fluorination include any of $CCl_3CH_2CH_2Cl$, $CCl_3CH_2CHCl_2$, and $CCl_3CH_2CCl_3$. Thus, for example. $CCl_3CH_2CH_2Cl$ can be reacted with HF to form $CF_3CH=CH_2$, and the fluorination product comprising $CF_3CH=CH$ can be used as the precursor stream for (a). $CCl_3CH_2CHCl_2$ can be reacted with HF to form $CF_3CH=CHCl$ and the fluorination product comprising $CF_3CH=CHCl$ can be used as the precursor stream for (a). $CCl_3CH_2CCl_3$ can be reacted with HF to form $CF_3CH=CCl_2$ and $CF_3CH_2CCl_2F$ and the fluorination product comprising $CF_3CH=CCl$, and $CF_3CH_2CCl_2F$ can be used as the precursor stream for (a). Of note are embodiments where the reactor effluent from the fluorination, comprising HCl, HF and the $CF_3CH=CZ_2$ compound(s), is fed to the chlorofluorination of (a).

The preparation of $CCl_3CH_2CH_2Cl$ is described in U.S. Pat. No. 4,605.802. The preparation of $CCl_3CH_2CHCl_2$ and $CCl_3CH_2CCl_3$ is described in International Patent Application No. WO 97/05089.

The fluorination reaction may be carried out in the liquid or vapor phase. The contacting of $CCl_3CH_2CClZ_2$ with HF in the liquid phase may be conducted in one of several ways. The process of the invention may be done in batch, semicontinuous. or continuous modes. In the batch mode. liquid $CCl_3CH_2CClZ_2$ and HF are combined in an autoclave or other suitable reaction vessel and heated to the desired temperature. Preferably, the process of the invention is carried out by feeding liquid $CCl_3CH_2CClZ_2$ to a reactor containing HF. or a mixture containing HF and fluorinated compounds formed by heating $CCl_3CH_2CClZ_2$ and HF. Alternatively, HF may be fed to a reactor containing $CCl_3CH_2CClZ_2$, or a mixture of $CCl_3CH_2CClZ_2$ and of fluorinated compounds formed by reacting HF and $CCl_3CH_2CClZ_2$. In a variation of this embodiment, both HF and $CCl_3CH_2CClZ_2$ may be fed concurrently in the desired stoichiometric ratio to a reactor containing a mixture of HF and fluorinated compounds formed by reacting HF and $CCl_3CH_2CClZ_2$.

Preferably, the reaction of HF with $CCl_3CHCClZ_2$ is carried out in the vapor phase in a heated tubular reactor. The reactor may be empty, but is preferably filled with a suitable packing such as Monel™ or Hastelloy™ nickel alloy turnings or wool, or other material inert to HCl and HF which allows efficient mixing of liquid $CCl_3CH_2CClZ_2$ and HF vapor. The $CCl_3CH_2CClZ_2$ feed rate is determined by the temperature and the degree of fluorination desired.

Suitable temperatures for the fluorination reaction are within the range of from about 80° C. to about 250° C., preferably from about 100° C. to about 200° C. Higher temperatures result in greater conversion of the $CCl_3CH_2CClZ_2$ and a greater degree of fluorination in the converted products. The degree of fluorination reflects the number of fluorine substituents that replace chlorine substituents in the $CCl_3CH_2CClZ_2$ starting material. For example, the product 3,3,3-trifluoro-1-propene represents a higher degree of fluorination than the product 1,3-dichloro-1,1-difluoropropane.

The pressure used in the fluorination reaction is not critical and in batch reactions is usually the autogenous pressure of the system at the reaction temperature. In a continuous process, typical reactor pressures are from about 20 psig (239 kPa) to about 1.000 psig (6.994 kPa).

In the preferred, vapor phase mode of the fluorination reaction, the reaction may be carried out at atmospheric pressure, or for reasons such as convenience of separations later in the process, pressures of up to 30 atmospheres may be employed.

The mole ratio of HF to $CCl_3CH_2CClZ_2$ in the fluorination reaction is typically from about 3:1 to about 75:1, and is preferably from about 3:1 to about 50:1. Ratios of about 8:1 to about 40:1 are most preferred as this eliminates the need for further addition of HF in subsequent reaction steps.

Examples of compounds produced in the fluorination reaction include $CF_3CH=CH_2$ (HFC-1243zf), $CF_3CH_2CH_2F$ (HFC-254fb), $CF_3CH=CHCl$ (HCFC-1233zd), $CF_3CH_2CHClF$ (HCFC-244fa), $CF_3CH=CCl_2$ (HCFC-1223za) and $CF_3CH_2CCl_2F$ (HCFC-234fb).

In addition, small amounts of other halogenated propanes may be formed having greater or lesser degrees of fluorination than the aforementioned products. Examples of products having a lower degree of fluorination than the aforementioned products include $CF_3CH_2CH_2Cl$ (HCFC-253fb), $CClF_2CH_2CH_2Cl$ (HCFC-252fb), $CCl_2FCH_2CH_2Cl$ (HCFC-251fc), $CClF_2CH=CH_2$ (HCFC-1242zf), $CF_3CH_2CHCl_2$ (HCFC-243fa), $CClF_2CH_2CHCl_2$ (HCFC-242fa), $CClF_2CH=CHCl$ (HCFC-1232zd), $CF_3CH_2CCl_3$ (HCFC-233fb), $CClFH_2CHClClF$ (HCFC-233fa), $CClF_2CH_2CCl_3$ (HCFC-232fb), $CCl_2FCH_2CCl_2F$ (HCFC-232fa), $CClFCH_2CCl_3$ (HCFC-231fa) and $CClFCH=CClF$ (HCFC-1222zb).

Examples of compounds produced in the fluorination reaction having a higher degree of fluorination than the aforementioned products include $CF_3CH=CHF$ (HFC-1234ze), $CF_3CH_2CHF_2$ (HFC-245fa), $CF_3CH=CClF$ (HCFC-1224zb), $CF_3CH=CF_2$ (HFC-1225zc), $CF_3CH)CClF_2$ (HCFC-235fa), and $CF_3CH_2CF_3$ (HFC-236fa).

A fluorination catalyst is not needed for the reaction of HF with $CCl_3CH_2CClZ_2$, but may be added if desired to increase the conversion of $CCl_3CH_2CClZ_2$, the rate of the reaction, or the degree of fluorination of the compounds produced. Liquid phase fluorination catalysts which may be used in the fluorination reaction include carbon, $AlF_3$, $BF_3$, $FeCl_{3-a}F_a$ (where a is 0 to 3), $FeZ_3$ (where Z is Cl, F or mixtures thereof) supported on carbon, $SbCl_{3-a}F_a$, $AsF_3$, $MCl_{5-b}F_b$ (where b is 0 to 5 and M is Sb, Nb, Ta, or Mo), and $M'Cl_{4-c}F_c$ (where c is 0 to 4, and M' is Sn, Ti, Zr, or Hf).

Vapor phase fluorination catalysts which may be used in the fluorination reaction include metal compounds (e.g., metal oxides. metal halides, and/or other metal salts). The metal compounds may be unsupported or supported. Suitable supports for the supported catalyst include alumina, aluminum fluoride, fluorided alumina and carbon.

Suitable metal compounds for use as catalysts (optionally on alumina, aluminum fluoride, fluorided alumina, or carbon) include those of chromium, iron, cobalt, nickel, manganese, magnesium, copper and zinc. Preferably when used on a support, the total metal content of the catalyst will be from about 0.1 to 20 percent by weight; typically from about 0.1 to 10 percent by weight.

Of note are chromium-containing catalysts (e.g., $Cr_2O_3$ by itself or with other metal compounds such as magnesium halides or zinc halides on $Cr_2O_3$); and mixtures of chromium-magnesium compounds (including metal oxides, metal halides. and/or other metal salts) optionally on graphite.

Fluorided alumina and aluminum fluoride can be prepared as described in U.S. Pat. No. 4,902,838. Metal compounds on aluminum fluoride and metal compounds on fluorided alumina can be prepared by procedures described in U.S. Pat. No. 4,766,260. Catalysts comprising chromium are well known in the art (see e.g., U.S. Pat. No. 5.036,036). Chromium compounds supported on alumina can be prepared as described in U.S. Pat. No. 3.541,834. Chromium compounds supported on carbon can be prepared as described in U.S. Pat. No. 3,632,834. Catalysts comprising chromium and magnesium compounds may be prepared as described in Canadian Patent No. 2,025,145. Other metal and magnesium compounds optionally on graphite can be prepared in a similar manner to the latter patent.

Preferably. a catalyst is not used in the fluorination reaction. Of particular note are embodiments where $CCl_3CH_2CH_2Cl$ is reacted with HF to form $CF_3CH=CH_2$ in a reactor which is free of added catalyst.

The feed to the chlorofluorination reaction zone includes the precursor stream as well as underfluorinated component (iii) from distillation (b).

In (a) of the process of the invention, the precursor stream of at least one compound selected from halogenated propanes of the formula $CX_3CH_2CH_yX_{(3-y)}$ and halogenated propenes of the formula $CX_3CH=CH_yX_{(2-y)}$, where each X is independently selected from Cl and F and y is 0, 1 or 2, provided that the average fluorine content of said precursor stream is no more than 5 fluorine substituents per molecule, is contacted with HF and chlorine ($Cl_2$) in a reaction zone for chlorofluorination.

Preferably, the contacting in (a) is carried out in the vapor phase in a heated tubular reactor. Prior to the reactor, a mixing zone, preferably filled with a suitable packing such as Monel™ or Hastelloy™ nickel alloy turnings or wool, or other material inert to HCl and HF may be employed to allow efficient mixing of HF, HCl, $CX_3CH_2CH_yX_{(3-y)}$, and $CX_3CH=CHyX_{(2-y)}$ vapor with chlorine. The flow rates in said tubular reactor in the chlorofluorination reaction zone are determined by the temperature and the degree of fluorination desired. A slower feed rate at a given temperature will increase contact time and tend to increase the amount of conversion of $CX_3CH_2CH_yX_{(3-y)}$, and $CX_3CH=CHY X_{(2-y)}$ and the amount of fluorine incorporated into the products.

Suitable temperatures for the chlorofluorination are in the range of from about 150° C. to about 400° C., preferably from about 200° C. to about 325° C. Higher temperatures result in greater conversion of $CX_3CH_2CH_yX_{(3-y)}$, and $CX_3CH=CH_yX_{(2-y)}$ and greater degrees of fluorination and chlorination in the converted products. The degree of chlorination reflects the number of chlorine substituents that replace hydrogen substituents in the starting materials. Said chlorine substituents themselves will be replaced by fluorine in the chlorofluorination reaction zone via the reaction of the chlorinated product with HF. For example, the product 1,1,2-trichloro-3,3,3-trifluoropropane (HCFC-233da) represents a higher degree of chlorination than the intermediate 1-chloro-3,3,3-trifluoro-1-propene (HCFC-12233zd).

Since the chlorofluorination reaction occurring in (a) is increasing the net number of halogen (i.e. chlorine and fluorine) substituents in the propane products, it is possible to refer to the degree of halogenation of the products which reflects the total number of chlorine and fluorine substituents that replace hydrogen substituents in the starting material. Thus, the product 2-chloro-1,1,1,2,3.3-hexafluoropropane (HCFC-226ba) represents a higher degree of halogenation than the intermediate 1,2-dichloro-3,3,3-trifluoropropane (HCFC-243db).

The pressure of the chlorofluorination reaction is not critical and may be in the range of from about 1 to about 30 atmospheres. A pressure of about 20 atmospheres may be advantageously employed to facilitate separation of HCl from other reaction products in (b).

The mole ratio of HF to $CX_3CH_2CH_yX_{(3-y)}$, and/or $CX_3CH=CH_yX_{(2-y)}$ in the chlorofluorination reaction is typically from about 3:1 to about 75:1, and is preferably from about 3:1 to about 50:1. Ratios of about 8:1 to about 40:1 are most preferred.

The ratio of $Cl_2$ to $CX_3CH_2CH_yX_{(3-y)}$, and/or $CX_3CH=CH_yX_{(2-y)}$, is typically from about 1:1 to about 10:1. The amount of chlorine fed to the chlorofluorination reaction zone in (a) also depends on the hydrogen content of the starting material is). If y is 0 in the above formulas, a 1:1 ratio of Cl to the starting material(s) is sufficient for the process of the invention. If y is 2 in the above formulas, then a 3:1 ratio of $Cl_2$ to the starting material(s) is sufficient for the process of the invention. A slight excess of chlorine over the stoichiometric amount may be necessary for practical reasons, but large excesses of chlorine such as 20:1 will result in complete chlorofluorination of the products which is not necessary for the process of the invention.

Examples of compounds that may be produced in the chlorofluorination reaction zone (a) include $CF_3CClFCHF_2$ (HCFC-226ba), $CF_3CHFCClF$, (HCFC-226ea), $CF_3CF_2CHClF$ (HCFC-226ca), $CF_3CHClCF_3$ (HCFC-226da), $CF_3CCl_2CF_3$ (CFC-216aa), and $CF_3CClFCClF_2$ (CFC-216ba).

In addition, small amounts of other halogenated propanes may be formed having greater degrees of fluorination. Examples of halogenated propanes having greater degrees of fluorination are $CF_3CClFCF_3$ (CFC-217ba), $CF_3CF_2CClF_2$ (CFC-217ca), $CF_3CHFCF_3$ (HFC-227ea), $CF_3CFCHF_2$ (HFC-227ca) and $CF_3CF_2CF_3$ (FC-218).

In addition small amounts of other halogenated propanes may be formed having lower degrees of fluorination and chlorination. Examples of products having lower degrees of fluorination and chlorination include $CF_3CCl_2CHF_2$ (HCFC-225aa), $CF_3CClFCHClF$ (HCFC-225ba), $CF_3CF_2CHCl_2$ (HCFC-225ca), $CF_3CHClCClF_2$ (HCFC-225da), $CF_3CHClCH_2Cl$ (HCFC-243db), $CF_3CClCClF_2$ (CFC-215aa), $CClFCClFCClF_2$ (CFC-215ba), $CF_3CClFCCl_2F$ (CFC-215bb), $CF_3CClCCl_2F$ (CFC-214ab), $CF_3CCl_2CHClF$ (HCFC-224aa), $CF_3CClFCHCl_2$ (HCFC-224ba), $CF_3CHClCCl_2F$ (HCFC-224db), $CF_3CClFCH_2Cl$ (HCFC-234bb), $CF_3CCl_2CH_2Cl$ (HCFC-233ab), $CF_3CHClCHCl_2$ (HCFC-233da), $CF_3CClCHCl_2$ (HCFC-223aa), $CF_3CHClCCl_3$ (HCFC-223db) and $CF_3CCl=CCl_2$ (CFC-1213xa).

Preferably the chlorofluorination reaction of (a) is done in the presence of a fluorination catalyst. Examples of fluorination catalysts suitable for the chlorofluorination in (a) include those described above in connection with $CCl_3CH_2CClZ_2$ fluorination reactions. Preferred vapor phase fluorination catalysts for (a) comprise trivalent chromium. Of particular note are $Cr_2O_3$ prepared by pyrolysis of $(NH_4)_2Cr_2O_7$, $Cr_2O_3$ having a surface area greater than about 200 m$^2$/g, and $Cr_2O_3$ prepared by pyrolysis of $(NH_4)_2Cr_2O_7$ or having a surface area greater than about 200 m$^2$/g which is pre-treated with a vaporizable fluorine-containing compound such as HF or a fluorocarbon such as $CCl_3F$. These pre-treated catalysts are most preferred.

The $Cr_2O_3$ catalyst prepared by the pyrolysis of ammonium dichromate suitable for (a) can be prepared by any method known to the art including those disclosed in U.S. Pat. Nos. 4,843,181 and 5,036,036 which are hereby incorporated herein by reference. Other $Cr_2O_3$ catalysts which may be used in (a) include catalysts having a surface area greater than about 200 m$^2$/g, some of which are commercially available.

Generally, the resulting $Cr_2O_3$ will be pretreated with HF. This pretreatment can be accomplished by placing $Cr_2O_3$ in a suitable container which can be the reactor to be used to perform the reaction described in (a) in the instant invention, and thereafter, passing HF over the dried $Cr_2O_3$ so as to partially saturate the $Cr_2O_3$ with HF. This is conveniently carried out by passing HF over the $Cr_2O_3$ for a period of time, for example. about 15 to 300 minutes at a temperature of, for example, about 200° C. to about 450° C. Nevertheless, this pretreatment is not essential.

In (b) of the process of the invention, the reaction zone effluent from (a) is distilled. Typically, more than one distillation column is employed. The effluent from (a) is delivered to a distillation column to produce a low-boiling component (i) comprising HCl and when they are present in the reaction zone effluent of (a) $CF_3CF_2CF_3$ (FC-218), $CClF_2CF_2CF_3$ (CFC-217ca), $CF_3CClFCF_3$ (CFC-217ba) $CHF_2CF_2CF_3$ (HFC-227ca) and $CF_3CHFCF_3$ (HFC-227ea). Any azeotropes of the above compounds with HCl or HF will also be in the low-boiling component.

It is noted that HFC-227ca and HFC-227ea are themselves valuable as fire extinguishants as disclosed in U.S. Pat. No. 5,084,190, and in refrigeration and heat transfer compositions as disclosed in U.S. Pat. No. 5,417,871 and in International Application No. WO 95/08603. Accordingly, CFC-217ca and CFC-217ba from the low-boiling component (i) can be reacted with hydrogen after separation to produce additional HFC-227ca and HFC-227ea respectively. The reaction of hydrogen with CFC-217ca and CFC-217ba is preferably carried out in the vapor phase at a temperature of at least about 100° C. and less than 500° C. over a metal-containing catalyst at a pressure of from about 100 kPa to about 7,000 kPa. Preferred catalysts for the hydrogenolysis of the C—Cl bonds in CFC-217ca and CFC-217ba include those described for $CClF_2CClFCF_3$ and $CHF_2CClFCF_3$ hydrogenation herein.

A hydrogenation feed component (ii) is also produced from the distillation process of (b). Components (ii) includes $CClF_2CClFCF_3$ (CFC-216ba) and $CHFlCClFCF_3$ (HCFC-226ba). Component (ii) also typically includes HF and one or more of $CF_3CHFCClF_2$ (HCFC-226ea). $CF_3CF_2CHClF$ (HCFC-226ca), and $CF_3CCl_2CF_3$ (CFC-216aa). It is normally preferable to adjust the chlorofluorination reaction temperatures such that the production of $CF_3CClFCHF_2$ and $CF_3CClFCClF_2$ is maximized. As illustrated in Examples 1 and 2, reaction temperatures above 300° C. can greatly increase the amount of $CF_3CCl_2CF_3$ and $CF_3CF_2CHF$ that are formed at the expense of HCFC-226ba and CFC-216ba. Accordingly, also of note are embodiments where the chlorofluorination of (a) produces $CF_3CCl_2CF_3$, and where the hydrogenation of (c) produces $CF_3CH_2CF_3$.

A third major fraction produced from the distillation (b) is an underfluorinated component (iii) comprising halogenated propanes containing at least one chlorine substituent and from one to five fluorine substituents. Examples of compounds in component (iii) include $CF_3CCl_2CHF_2$ (HCFC-225aa), $CF_3CClFCHClF$ (HCFC-225ba), $CF_3CF_2CHCl_2$ (HCFC-225ca), $CF_3CHClCClF_2$ (HCFC-225da), $CF_3CHClCH_2Cl$ (HCFC-243db), $CF_3CCl_2CClF_2$ (CFC-215aa), $CClF_2CClFCClF_2$ (CFC-215ba), $CF_3CClFCCl_2F$ (CFC-215bb), $CF_3CClCCl_2F$ (CFC-214ab), $CF_3CCl_2CHClF$ (HCFC-224aa), $CF_3CClFCHCl_2$ (HCFC-224ba), $CF_3CHClCCl_2F$ (HCFC-224db), $CF_3CClFCH_2Cl$ (HCFC-234bb), $CF_3CCl_2CH_2Cl$ (HCFC-233ab), $CF_3CHClCHCl_2$ (HCFC-233da), $CF_3CCl_2CHCl_2$ (HCFC-223aa), $CF_3CHClCCl_3$ (HCFC-223db) and $CF_3CCl=CCl_2$ (CFC-1213xa).

In (c) of the process of the invention, the hydrogenation feed component (ii) removed from the distillation column in (b) is reacted with hydrogen ($H_2$) in a reaction zone. The hydrogenation feed component (ii) can comprise a mixture of HF, $CF_3CClFCHF_2$ (HCFC-226ba), $CF_3CHFCClF)$ (HCFC-226ea), $CF_3CF_2CHClF$ (HCFC-226ca), $CF_3CCl_2CF_3$ (CFC-216aa), and $CF_3CClFCClF_2$ (CFC-216ba).

The reaction in (c) is carried out in the vapor phase. Suitable temperatures for the reaction in (c) are in the range of from about 100° C. to about 400° C., preferably from about 150° C. to about 350° C. Higher temperatures result in greater conversion of $CF_3CClFCHF_2$ (HCFC-226ba). $CF_3CHFCClF_2$ (HCFC-226ea), $CF_3CF_2CHClF$ (HCFC-226ca), $CF_3CCl_2CF_3$ (CFC-216aa), and $CF_3CClFCClF_2$ (CFC-216ba).

The pressure used in (c) is not critical and may be in the range of from about 1 to 30 atmospheres. A pressure of about 20 atmospheres may be advantageously employed to facilitate separation of HCl from other reaction products.

The amount of hydrogen ($H_2$) fed to (c) is based on the total amount of $CF_3CClFCHF_2$ (HCFC-226ba), $CF_3CHFCClF_2$ (HCFC-226ea), $CF_3CF_2CHClF$ (HCFC-226ca). $CF_3CCl_2CF_3$ (CFC-216aa), and $CF_3CClFCClF_2$ (CFC-216ba) fed to the reaction zone. The ratio of $H_2$ to $CF_3CClFCHF_2$ (HCFC-226ba), $CF_3CHFCClF_2$ (HCFC-226ea), $CF_3CF_2CHClF$ (HCFC-226ca), $CF_3CCl_2CF_3$ (CFC-216aa). and $CF_3CClFCClF_2$ (CFC-216ba) is typically in the range of from about 1:1 to about 20:1, preferably from about 2:1 to about 10:1.

Compounds produced in the reaction zone in step (c) ordinarily include $CF_3CF=CF_2$ (HFP) and $CF_3CH_2CF_3$ (HFC-236fa). In addition, small amounts of $CF_3CHFCHF_2$ (HFC-236ea), $CF_3CFCH_2F$ (HFC-236cb) and $CF_3CHClCF_3$ (HCFC-226da) will typically be formed.

Preferably the reaction in (c) takes place in the presence of a catalyst. Suitable catalysts for (c) include iron, rhenium, ruthenium, osmium, cobalt, rhodium, iridium, nickel, palladium, and platinum. Said catalysts are preferably supported on carbon, a metal oxide such as alumina or chromia, fluorided alumina or a metal halide such as $AlF_3$, $CrF_3$ or $MgF_2$. Preparation of carbon-supported palladium catalysts are described in U.S. Pat. No. 5,523,501.

Especially preferred catalysts for (c) are those containing rhenium and/or ruthenium. The catalysts containing rhenium and/or ruthenium may or may not be supported. Preferred supports are carbon, alumina, aluminum fluoride and fluorided alumina. Preparation of supported rhenium catalysts are described in U.S. Pat. No. 5,068,473. Particular ruthenium-containing catalysts are disclosed in PCT International Publication No. WO 97/19751.

In (d) of the process of the invention, $CF_3CF=CF_2$ produced in step (c), is recovered. Optionally, $CF_3CH_2CF_3$ (HFC-236fa), and $CF_3CHFCHF_2$ (HFC-236ea) may also be recovered. These compounds are typically recovered by distillation individually or as their HF azeotropes. HF may be removed from these compounds by conventional means such as scrubbing with base or by azeotropic distillation.

In (e) of the process of the invention, the underfluorinated component (iii) of (b) is returned to (a) for furter chlorofluorination.

FIG. 1 is illustrative of one method of practicing this invention. Referring to FIG. 1. a feed mixture comprising HF and $CCl_3CH_2CClZ_2$, where each Z is independently selected from the group H and Cl, and where the mole ratio of HF:$CCl_3CH_2CClZ_2$ is about 3:1 or more, is passed through line (110) into reactor (100). The reaction temperature is at least 80° C. but not more than 250° C.

The reactor effluent from fluorination reactor (100) comprising HF, HCl, $CF_3CH=CZ_2$, and $CF_3CH_2CZ_2F$ is passed through line (120) into line (420) where it is combined with the column bottoms from distillation column (400). The column (400) bottoms comprise $C_3Z_{3+z}F_{5-z}$ where z is 0, 1 or 2. Examples of compounds having the formula $C_3Z_{3+z}F_{5-z}$ include $CF_3CCl_2CHF_2$ (HCFC-225aa), $CF_3CClFCHClF$ (HCFC-225ba), $CF_3CF_2CHCl_2$ (HCFC-225ca), $CF_3CHClCClF_2$ (HCFC-225da), $CF_3CHClCH_2Cl$ (HCFC-243db), $CF_3CCl_2CClF_2$ (CFC-215aa), $CClF_2CClFCClF_2$ (CFC-215ba), $CF_3CClFCCl_2F$ (CFC-215bb), $CF_3CClCClF$ (HCFC-214ab), $CF_3CCl_2CHClF$ (HCFC-224aa), $CF_3CClFCHCl_2$ (HCFC-224ba), $CF_3CHClCCl_2F$ HCFC-224db), $CF_3CClFCH_2Cl$ (HCFC-234bb), $CF_3CCl.CH)Cl$ (HCFC-233ab). $CF_3CHClCHCl_2$ (HCFC-233da), $CF_3CCl_2CHCl_2$ (HCFC-223aa) and $CF_3CHClCCl_3$ (HCFC-223db).

The combined reactor (100) effluent and distillation column (400) bottoms are sent to reactor (200) which is maintained at a temperature within the range of about 150° C. to about 350° C. Reactor (200) is packed with a fluorination catalyst. A preferred catalyst is $Cr_2O_3$ prepared by the pyrolysis of $(NH_4)_2Cr_2O_7$ as described in U.S. Pat. No.

5,036,036. Chlorine is fed into the reactor (200) through line (210). The amount of chlorine fed to reactor (200) is based on the amount of $CCl_3CH_2CClX_2$ fed to reactor (100) and the amount of $C_3Z_{3+z}F_{5-z}$ recycled. The mole ratio of $Cl_2$:$CCl_3CH_2CClX_2$ is within the range of about 1:1 to about 10:1. Additional HF may be added. if required.

The chlorofluorination reactor (200) effluent comprising HF, HCl, $CF_3CClFCHF_2$, $CF_3CHFCClF_2$, $CF_3CClFCClF_2$, $CF_3CCl_2CF_3$, and a mixture of $C_3ZF_7$ and $C_3Z_{3+z}F_{5-z}$ where z is 0, 1 or 2, is sent through line (220) into distillation column (300). HCl, $C_3HF_7$, $C_3ClF_7$, $C_3F_8$ and any azeotropes of HCl or HF with $C_3HF_7$, $C_3ClF_7$ or $C_3F_8$ are removed through line (320) from the reactor (200) effluent and the remaining components of the reactor (200) effluent is sent through line (310) into a second distillation column (400).

HF, $CF_3CClFCHF_2$, $CF_3CHFCClF_2$, $CF_3CClFCClF_2$, and $CF_3CCl_2CF_3$ are removed from the top of column (400) through line (410) and sent to reactor (500) along with hydrogen, which is fed through line (510). The reactor (500) product is removed through line (520) and comprises. HCl, HF, hexafluoropropylene (i.e., $CF_3CF=CF_2$ or HFP), 1,1,1,3,3,3-hexafluoropropane ($CF_3CH_2CF_3$ or HFC-236fa) and 1,1,2,3,3,3-hexafluoropropane (HFC-236ea). HFP, HFC-236fa and HFC-236ea can be isolated by conventional means. The bottom fraction from column (400) which comprises $C_3Z_{3+z}F_{5-z}$ where z is as defined above is sent through line (420) into reactor (200).

Those skilled in the art will recognize that since the drawings are representational. it will be necessary to include further items of equipment in an actual commercial plant. such as pressure and temperature sensors, pressure relief and control valves. compressors, pumps, storage tanks and the like. The provision of such ancillary items of equipment would be in accordance with conventional chemical engineering practice.

The reactors used for this process and their associated feed lines. effluent lines. and other associated units should be constructed of materials resistant to hydrogen fluoride and hydrogen chloride. Typical materials of construction, well-known to the fluorination art, include stainless steels. in particular of the austenitic type. the well-known high nickel alloys. such as Monel T nickel-copper alloys. Hastelloy™ nickel-based alloys and Inconel™ nickel-chromium alloys, and copper-clad steel.

Without further elaboration it is believed that one skilled in the art can, using the description herein. utilize the present invention to its fullest extent. The following embodiments are, therefore, to be construed as merely illustrative, and do not constrain the remainder of the disclosure in any way whatsoever.

LEGEND

| | |
|---|---|
| 114a is $CCl_2FCF_3$ | 115 is $CClF_2CF_3$ |
| 214ab is $CCl_3FCCl_2CF_3$ | 215aa is $CClF_2CCl_2CF_3$ |
| 215ba is $CClF_2CClFCClF_2$ | 215bb is $CCl_2FCClFCF_3$ |
| 216aa-is-$CF_3CCl_2CF_3$ | 216ba is $CClF_2CClFCF_3$ |
| 216ca is $CClF_2CF_2CClF_2$ | 216cb is $CF_3CF_2CCl_2F$ |
| 217ba is $CF_3CClFCF_3$ | 217ca is $CClF_2CF_2CF_3$ |
| 218 is $CF_3CF_2CF_3$ | 223aa is $CF_3CCl_2CHCl_2$ |
| 224aa is $CF_3CCl_2CHClF$ | 224ba is $CF_3CClFCHCl_2$ |
| 225aa is $CHF_2Cl_2CF_3$ | 225ba is $CHClFCClFCF_3$ |
| 225ca is $CHCl_2CF_2CF_3$ | 226ba is $CF_3CClFCHF_2$ |
| 226ca is $CF_3CF_2CHClF$ | 226da is $CF_3CHClCF_3$ |
| 226ea is $CClF_2CHFCF_3$ | 227ca is $CF_3CF_2CHF_2$ |

-continued

LEGEND

| | |
|---|---|
| 227ea is $CF_3CHFCF_3$ | 232 is $C_3H_2Cl_4F_2$ |
| 233ab is $CF_3CCl_2CH_2Cl$ | 233da is $CF_3CHClCHCl_2$ |
| 234 is $C_3H_2Cl_2F_4$ | 234bb is $CF_3CClFCH_2Cl$ |
| 234da is $CF_3CHClCHClF$ | 235cb is $CF_3CF_2CH_2Cl$ |
| 235da is $CF_3CHClCHF_2$ | 236fa is $CF_3CH_2CF_3$ |
| 242 is $C_3H_3Cl_3F_2$ | 243db is $CF_3CHClCH_2Cl$ |
| 244 is $C_3H_3ClF_4$ | 245fa is $CF_3CH_2CHF_2$ |
| 252 is $C_3H_4Cl_2F_2$ | 1213xa is $CCl_2=CClCF_3$ |
| 1214 is $C_3Cl_2F_4$ | 1215 is $C_3ClF_5$ |
| 1222 is $C_3HCl_3F_2$ | 1223 is $C_3HCl_2F$ |
| 1224 is $C_3HClF_4$ | 1231 is $C_3H_2Cl_3F$ |
| 1232 is $C_3H_2Cl_2F_2$ | 1233xf is $CH_2=CClCF_3$ |
| 1233zd is $CHCl=CHCF_3$ | 1234 is $C_3H_2F_4$ |
| 1234ye is $CHF=CFCHF_2$ | 1234ze is $CHF=CHCF_3$ |
| 1243 is $C_3H_3F_3$ | 1243zf is $CH_2=CHCF_3$ |
| CT is contact time | |

General Procedure for Product Analysis

The following general procedure is illustrative of the method used. Part of the total reactor effluent was sampled on-line for organic product analysis using a Hewlett Packard HP 5890 gas chromatograph equipped with a 20 ft. (6.1 m) long×⅛ in. (0.32 cm) diameter tubing containing Krytox® perfluorinated polyether on an inert carbon support. The helium flow was 30 mL/min. Gas chromatographic conditions were 60° C. for an initial hold period of three minutes followed by temperature programming to 200° C. at a rate of 6° C./minute.

The bulk of the reactor effluent containing organic products and also inorganic acids such as HCl and HF was treated with aqueous caustic prior to disposal.

EXAMPLE 1

Chlorofluorination of $CCl_3CH_2CH_2Cl$

Chromium oxide (40.0 g, 30 mL, −12 to +20 mesh, (1.68 to 0.84 mm)), obtained from the pyrolysis of ammonium dichromate prepared according to the procedure described in U.S. Pat. No. 5,036,036, was placed in a ⅝" (1.58 cm) diameter Inconel™ nickel alloy reactor tube heated in a fluidized sand bath. The catalyst was heated from 60° C. to 175° C. in a flow of nitrogen (50 cc/min) over the course of about one hour. HF was then admitted to the reactor at a flow rate of 50 cc/min. After 35 minutes. the nitrogen flow was decreased to 20 cc/min and the HF flow increased to 80 cc/min. The reactor temperature was gradually increased to 400° C. during a three hour period and maintained at 400° C. for an additional 55 minutes. At the end of this period, the HF flow was stopped and the reactor cooled to 250° C. under 20 sccm (3.3×10⁻⁷ m³/s) nitrogen flow.

The results of the chlorofluorination of $CCl_3CH_2CH_2Cl$ are shown in Table 1; analytical data is given in units of GC area %. Total gas flow in the reactor was 120 sccm (2.0×10⁻⁶ m³/s) for a 15 second contact time except for the data at 400° C. which was conducted with a 30 second contact time.

TABLE 1

| T °C. | Molar Ratio HF:250fb:Cl$_2$ | C.T. Sec. | % 1243zf | % 242 | % 243db | % 244** | % 234bb | % 224aa | % 224ba |
|---|---|---|---|---|---|---|---|---|---|
| 170 | 20:1:0 | nc | 97.5 | 0 | 0 | 0.1 | 0 | 0 | 0 |
| 200 | 30:1:6 | nc | 35.4 | 4.2 | 34.9 | 2.6 | 0 | 0 | 0 |
| 200 | 30:1:6 | 15 | 0.1 | 0 | 55.3 | 7.1 | 6.7* | 4.2 | 0 |
| 225 | 30:1:6 | 15 | 0 | 0 | 10.6 | 3.1 | 19.0 | 20.0 | 0 |
| 250 | 30:1:6 | 15 | 0 | 0 | 0 | 0 | 0.8 | 31.7 | 25.3 |
| 275 | 30:1:6 | 15 | 0 | 0 | 0 | 0 | 0 | 3.1 | 4.6 |
| 300 | 30:1:6 | 15 | 0 | 0 | 0 | 0 | 0 | 0.5 | 0.7 |
| 325 | 30:1:6 | 15 | 0 | 0 | 0 | 0 | 0 | 0.3 | 0.3 |
| 350 | 30:1:6 | 15 | 0 | 0 | 0 | 0 | 0 | 0 | 0 |
| 375 | 30:1:6 | 15 | 0 | 0 | 0 | 0 | 0 | 0 | 0 |
| 400 | 30:1:6 | 30 | 0 | 0 | 0 | 0 | 0 | 0 | 0 | nc = no catalyst; reactants mixed in tube packed with Monel gauze (not exposed to the fluorination catalyst)
*Includes 1.7% of unidentified isomer
*Sum of two isomers

| T °C. | % 1233zd | % 1233xf | % 233ab | % 223aa | % 1213xa | % 1214* | % 215aa** | % 225aa | % 225ba |
|---|---|---|---|---|---|---|---|---|---|
| 170 | 0 | 0 | 0 | 0 | 0 | 0 | 0 | 0 | 0 |
| 200 | 4.6 | 4.0 | 3.2 | 2.5 | 0 | 0 | 0 | 0 | 0 |
| 200 | 5.8 | 1.5 | 10.7 | 0.5 | 2.4 | 0 | 0 | 0.1 | 0 |
| 225 | 1.3 | 0.4 | 32.0 | 2.1 | 6.8 | 0 | 0 | 0.4 | 0.5 |
| 250 | 0.1 | 0.1 | 0.3 | 0 | 6.5 | 4.3 | 2.8 | 7.1 | 18.8 |
| 275 | 0 | 0 | 0 | 0 | 0.5 | 0.2 | 7.0 | 37.3 | 18.7 |
| 300 | 0 | 0 | 0 | 0 | 0.1 | 0 | 7.4 | 26.3 | 3.3 |
| 325 | 0 | 0 | 0 | 0 | 0.1 | 0 | 8.9 | 5.2 | 1.2 |
| 350 | 0 | 0 | 0 | 0 | 0 | 0 | 0.8 | 1.1 | 0.2 |
| 375 | 0 | 0 | 0 | 0 | 0 | 0 | 0.9 | 0.6 | 0.2 |
| 400 | 0 | 0 | 0 | 0 | 0 | 0 | 0.2 | 0.2 | 0 |

*sum of two isomers
*includes <1% of an unidentified isomer

| T °C. | % 225ca | % 226ba | % 226ca | % 216ba | % 216aa | % 217ba | % 217ca | % 227ca | % 218 |
|---|---|---|---|---|---|---|---|---|---|
| 170 | 0 | 0 | 0 | 0 | 0 | 0 | 0 | 0 | 0 |
| 200 | 0 | 0 | 0 | 0 | 0 | 0 | 0 | 0 | 0 |
| 200 | 0 | 0 | 0 | 0 | 0 | 0 | 0 | 0 | 0 |
| 225 | 0 | 0 | 0 | 0 | 0 | 0 | 0 | 0 | 0 |
| 250 | 0 | 0.6 | 0 | 0.1 | 0.2 | 0 | 0 | 0 | 0 |
| 275 | 4.2 | 14.7 | 4.4 | 1.7 | 1.2 | 0.1 | 0 | 0.4 | 0 |
| 300 | 3.4 | 31.2 | 7.7 | 2.4 | 4.4 | 0.5 | 1.1 | 9.0 | 0 |
| 325 | 3.3 | 24.3 | 5.3 | 3.8 | 16.1 | 1.1 | 3.8 | 24.5 | 0 |
| 350 | 0.9 | 10.7 | 3.4 | 3.2 | 25.2 | 6.1 | 7.4 | 39.4 | 0.4 |
| 375 | 1.6 | 2.1 | 3.3 | 2.9 | 45.5 | 7.6 | 12.9 | 19.9 | 1.2 |
| 400 | 0.4 | 0.9 | 1.3 | 0.8 | 59.4 | 15.0 | 6.4 | 9.7 | 4.7 |

Other compounds observed at low levels include: 216cb, 226da, 232, 235cb, 245fa, 252, 1222, 1223, 1232, 1234ye, 1234ze.

EXAMPLE 2

Chlorofluorination of CCl$_3$CH$_2$CHCl$_2$

A fresh charge of chromium oxide (40.0 g, 30 mL, −12 to +20 mesh, (1.68 to 0.84 mm)) was loaded in the reactor and activated with HF following the procedure described in Example 1.

The results of the chlorofluorination of CCl$_3$CH$_2$CHCl$_2$ are shown in Table 2; analytical data is given in units of GC area %. Total gas flow in the reactor was 120 sccm (2.0×10$^{-6}$ m$^3$/s) for a 15 second contact time except for the data at 400° C. which was conducted with a 30 second contact time.

TABLE 2

| T °C. | Molar Ratio HF:240fa:Cl$_2$ | C.T. Sec. | % 1234* | % 1243 | % 242 | % 244 | % 234da* | % 224aa | % 224ba |
|---|---|---|---|---|---|---|---|---|---|
| 200 | 20:1:0 | nc | 2.7 | 0.1 | 0.2 | 0.3 | 0 | 0 | 0 |
| 200 | 30:1:6 | nc | 4.5 | 0 | 4.2 | 2.6 | 1.4 | 0 | 0 |
| 225 | 30:1:6 | 15 | 0 | 0 | 0 | 0 | 0 | 47.4 | 22.0 |
| 250 | 30:1:6 | 15 | 0 | 0 | 0 | 0 | 0 | 21.1 | 23.8 |
| 275 | 30:1:6 | 15 | 0 | 0 | 0 | 0 | 0 | 1.6 | 2.6 |
| 300 | 30:1:6 | 15 | 0 | 0 | 0 | 0 | 0 | 0.4 | 0.6 |
| 325 | 30:1:6 | 15 | 0 | 0 | 0 | 0 | 0 | 0.2 | 0.3 |
| 350 | 30:1:6 | 15 | 0 | 0 | 0 | 0 | 0 | 0.06 | 0.09 |

TABLE 2-continued

| | | | | | | | | | |
|---|---|---|---|---|---|---|---|---|---|
| 375 | 30:1:6 | 15 | 0 | 0 | 0 | 0 | 0 | 0 | 0 |
| 400 | 30:1:6 | 30 | 0 | 0 | 0 | 0 | 0 | 0 | 0 |

| T °C. | % 1223* | % 1233zd* | % 233da | % 223aa | % 1224* | % 235da | % 1213xa | % 1214 |
|---|---|---|---|---|---|---|---|---|
| 200 | 0 | 96.6 | 0 | 0 | 0 | 0 | 0 | 0 |
| 200 | 6.6 | 77.0 | 8.0 | 0 | 0 | 0 | 0 | 0 |
| 225 | 1.8 | 0 | 0 | 4.5 | 0.95 | 13.0 | 0.3 | 0 |
| 250 | 0 | 0 | 0 | 0.7 | 1.0 | 2.0 | 0 | 1.3 |
| 275 | 0 | 0 | 0 | 0 | 0.1 | 0 | 0 | 0 |
| 300 | 0 | 0 | 0 | 0 | 0.2 | 0 | 0 | 0 |
| 325 | 0 | 0 | 0 | 0 | 0 | 0 | 0 | 0 |
| 350 | 0 | 0 | 0 | 0 | 0 | 0 | 0 | 0 |
| 375 | 0 | 0 | 0 | 0 | 0 | 0 | 0 | 0 |
| 400 | 0 | 0 | 0 | 0 | 0 | 0 | 0 | 0 |

| T °C. | % 214ab | % 215ba/bb | % 215aa | % 225aa | % 225ba* | % 225ca | % 216ca/cb | % 226da |
|---|---|---|---|---|---|---|---|---|
| 200 | 0 | 0 | 0 | 0 | 0 | 0 | 0 | 0 |
| 200 | 0 | 0 | 0 | 0 | 0 | 0 | 0 | 0 |
| 225 | 0.3 | 0.3 | 0.9 | 4.6 | 2.6 | 0 | 0 | 0 |
| 250 | 0 | 1.0 | 2.8 | 14.8 | 28.7 | 0 | 0 | 0 |
| 275 | 0 | 0.2 | 6.0 | 42.3 | 13.8 | 3.8 | 0.5 | 0.3 |
| 300 | 0 | 0 | 6.8 | 24.4 | 3.2 | 2.4 | 0.6 | 0.6 |
| 325 | 0 | 0 | 8.4 | 5.1 | 1.1 | 2.2 | 0.5 | 0.5 |
| 350 | 0 | 0 | 2.0 | 1.4 | 0.4 | 1.7 | 0.4 | 0.1 |
| 375 | 0 | 0 | 0.02 | 0.08 | 0 | 0 | 0.1 | 0.03 |
| 400 | 0 | 0 | 0.2 | 0 | 0 | 0.06 | 0.2 | 0 |

| T °C. | % 226ba | % 226ca | % 216ba | % 216aa | % 217ba | % 217ca | % 227ca | % 218 |
|---|---|---|---|---|---|---|---|---|
| 200 | 0 | 0 | 0 | 0 | 0 | 0 | 0 | 0 |
| 200 | 0 | 0 | 0 | 0 | 0 | 0 | 0 | 0 |
| 225 | 0 | 0 | 0 | 0 | 0 | 0 | 0 | 0 |
| 250 | 1.4 | 0.09 | 0.4 | 0.3 | 0 | 0 | 0 | 0 |
| 275 | 17.9 | 5.9 | 2.2 | 1.5 | 0.1 | 0.08 | 0.7 | 0 |
| 300 | 33.8 | 6.7 | 2.7 | 5.1 | 0.4 | 1.2 | 10.3 | 0 |
| 325 | 26.1 | 4.8 | 4.1 | 16.6 | 0.97 | 3.9 | 24.7 | 0.04 |
| 350 | 7.8 | 4.3 | 4.4 | 32.5 | 3.5 | 8.5 | 32.1 | 0.3 |
| 375 | 5.4 | 0.5 | 2.2 | 35.1 | 11.6 | 9.6 | 32.6 | 1.8 |
| 400 | 0.2 | 0.2 | 0.8 | 64.4 | 16.7 | 9.1 | 1.6 | 6.2 | nc = no catalyst; reactants mixed in tube packed with Monel gauze (not exposed to the fluorination catalyst)
*sum of two isomers
Other compounds observed at low levels include: 114a, 115, 236fa, 1215, 1231

What is claimed is:

1. A process for the manufacture of $CF_3CF=CF_2$, and optionally at least one compound selected from $CF_3CH_2CF_3$ and $CF_3CHFCHF_2$, comprising:
   (a) contacting a reactor feed comprising precursor stream of at least one compound selected from halogenated propanes of the formula $CX_3CH_2CH_yX_{(3-y)}$ and halogenated propenes of the formula $CX_3CH=CH_yX_{(2-y)}$, where each X is independently selected from Cl and F and y is 0, 1 or 2, provided that the average fluorine content of said precursor stream is no more than 5 fluorine substituents per molecule, with HF and $Cl_2$ in a chlorofluorination reaction zone containing a fluorination catalyst and operating at a temperature between about 150° C. and 400° C. to produce a reaction zone effluent comprising HF, HCl and a mixture of reaction products of said precursor stream which contains at least one compound of the formula $C_3Cl_2F_6$ including $CClF_2CClFCF_3$ and at least one compound of the formula $C_3HClF_6$ including $CHF_2CClFCF_3$ and has an average fluorine content which is at least one fluorine substituent per molecule more than the average fluorine content of the precursor stream;
   (b) distilling the reaction zone effluent of (a) to produce (i) a low-boiling component comprising HCl and when they are present in said reaction zone effluent, $C_3F_8$, $C_3ClF_7$ and $C_3HF_7$, (ii) a hydrogenation feed component comprising at least one compound of the formula $C_3Cl_2F_6$ including $CClF_2CClFCF_3$ and at least one compound of the formula $C_3HClF_6$ including $CHF_2CClFCF_3$, and (iii) an underfluorinated component comprising halogenated propanes containing at least one chlorine substituent and from one to five fluorine substituents;
   (c) reacting the $CClF_2CClFCF_3$ and $CHF_2CClFCF_3$ of hydrogenation feed component (ii) with hydrogen to produce a mixture comprising $CF_3CF=CF_2$ and $CF_3CHFCHF_2$;
   (d) recovering the $CF_3CF=CF_2$ from the product mixture of (c); and
   (e) returning the underfluorinated component (iii) to the chlorofluorination reaction zone.

2. The process of claim 1 wherein $CCl_3CH_2CH_2Cl$ is reacted with HF to form $CF_3CH=CH_2$, and the fluorination product comprising $CF_3CH=CH_2$ is used as the precursor stream for (a).

3. The process of claim 2 wherein the $CCl_3CH_2CH_2Cl$ is reacted in a reactor which is free of added catalyst.

4. The process of claim 1 wherein $CCl_3CH_2CHCl_2$ is reacted with HF to form $CF_3CH=CHCl$, and the fluorination product comprising $CF_3CH=CHCl$ is used as the precursor stream for (a).

5. The process of claim 1 wherein $CCl_3CH_2CCl_3$ is reacted with HF to form $CF_3CH=CCl_2$ and $CF_3CH_2CCl_2F$ and the fluorination product comprising $CF_3CH=CCl_2$ and $CF_3CH_2CCl_2F$ is used as the precursor stream for (a).

6. The process of claim 1 wherein $CF_3CCl_2CF_3$ is produced in (a), and $CF_3CH_2CF_3$ is produced in (c).

7. The process of claim 1 wherein the catalyst of (a) comprises trivalent chromium.

8. The process of claim 1 wherein the reaction of (c) is conducted in the presence of a catalyst containing at least one of rhenium and ruthenium.

9. A process for the manufacture of $CF_3CF=CF_2$, and optionally at least one compound selected from $CF_3CH_2CF_3$ and $CF_3CHFCHF_2$, comprising:

(a) contacting a reactor feed comprising precursor stream of at least one compound selected from halogenated propanes of the formula $CX_3CH_2CH_yX_{(3-y)}$ and halogenated propenes of the formula $CX_3CH=C_yX_{(2-y)}$, where each X is independently selected from Cl and F and y is 0, 1 or 2, provided that the average fluorine content of said precursor stream is no more than 5 fluorine substituents per molecule, with HF and $Cl_2$ in a chlorofluorination reaction zone containing a fluorination catalyst and operating at a temperature between about 150° C. and 325° C., to produce a reaction zone effluent comprising HF, HCl and a mixture of reaction products of said precursor stream which contains at least one compound of the formula $C_3Cl_2F_6$ including $CClF_2CClFCF_3$ and at least one compound of the formula $C_3HClF_6$ including $CHF_2CClFCF_3$ and has an average fluorine content which is at least one fluorine substituent per molecule more than the average fluorine content of the precursor stream;

(b) distilling the reaction zone effluent of (a) to produce (i) a low-boiling component comprising HCl and when they are present in said reaction zone effluent, $C_3F_8$, $C_3ClF_7$ and $C_3HF_7$, (ii) a hydrogenation feed component comprising at least one compound of the formula $C_3Cl_2F_6$ including $CClF_2CClFCF_3$ and at least one compound of the formula $C_3HClF_6$ including $CHF_2CClFCF_3$, and (iii) an underfluorinated component comprising halogenated propanes containing at least one chlorine substituent and from one to five fluorine substituents;

(c) reacting the $CClF_2CClFCF_3$ and $CHF_2CClFCF_3$ of hydrogenation feed component (ii) with hydrogen to produce a mixture comprising $CF_3CF=CF_2$ and $CF_3CHFCHF_2$;

(d) recovering the $CF_3CF=CF_2$ from the product mixture of (c); and (e) returning the underfluorinated component (iii) to the chlorofluorination reaction zone.

10. The process of claim 9 wherein $CCl_3CH_2CH_2Cl$ is reacted with HF to form $CF_3CH=CH_2$, and the fluorination product comprising $CF_3CH=CH_2$ is used as the precursor stream for (a).

11. The process of claim 10 wherein the $CCl_3CH_2CH_2Cl$ is reacted in a reactor which is free of added catalyst.

12. The process of claim 9 wherein $CCl_3CH_2CHCl_2$ is reacted with HF to form $CF_3CH=CHCl$, and the fluorination product comprising $CF_3CH=CHCl$ is used as the precursor stream for (a).

13. The process of claim 9 wherein $CCl_3CH_2CCl_3$ is reacted with HF to form $CF_3CH=CCl_2$ and $CF_3CH_2CCl_2F$ and the fluorination product comprising $CF_3CH=CCl_2$ and $CF_3CH_2CCl_2F$ is used as the precursor stream for (a).

14. The process of claim 9 wherein $CF_3CCl_2CF_3$ is produced in (a), and $CF_3CH_2CF_3$ is produced in (c).

15. A process for the manufacture of $CF_3CF=CF_2$, and at least one compound selected from $CF_3CH_2CF_3$ and $CF_3CHFCHF_2$, comprising:

(a) contacting a reactor feed comprising precursor stream of at least one compound selected from halogenated propanes of the formula $CX_3CH_2CH_yX_{(3-y)}$ and halogenated propenes of the formula $CX_3CH=CH_yX_{(2-y)}$, where each X is independently selected from Cl and F and y is 0, 1 or 2, provided that the average fluorine content of said precursor stream is no more than 5 fluorine substituents per molecule, with HF and $Cl_2$ in a chlorofluorination reaction zone containing a fluorination catalyst and operating at a temperature between about 150° C. and 400° C., to produce a reaction zone effluent comprising HF, HCl and a mixture of reaction products of said precursor stream which contains at least one compound of the formula $C_3Cl_2F_6$ including $CClF_2CClFCF_3$ and at least one compound of the formula $C_3HClF_6$ including $CHF_2CClFCF_3$ and has an average fluorine content which is at least one fluorine substituent per molecule more than the average fluorine content of the precursor stream;

(b) distilling the reaction zone effluent of (a) to produce (i) a low-boiling component comprising HCl and when they are present in said reaction zone effluent, $C_3F_8$, $C_3ClF_7$ and $C_3HF_7$, (ii) a hydrogenation feed component comprising at least one compound of the formula $C_3Cl_2F_6$ including $CClF_2CClFCF_3$ and at least one compound of the formula $C_3HClF_6$ including $CHF_2CClFCF_3$, and (iii) an underfluorinated component comprising halogenated propanes containing at least one chlorine substituent and from one to five fluorine substituents;

(c) reacting the $CClF_2CClFCF_3$ and $CHF_2CClFCF_3$ of hydrogenation feed component (ii) with hydrogen to produce a mixture comprising $CF_3CF=CF_2$ and $CF_3CHFCHF_2$;

(d) recovering the $CF_3CF=CF_2$ from the product mixture of (c); and (e) returning the underfluorinated component (iii) to the chlorofluorination reaction zone.

16. The process of claim 15 wherein $CCl_3CH_2CH_2Cl$ is reacted with HF to form $CF_3CH=CH_2$, and the fluorination product comprising $CF_3CH=CH_2$ is used as the precursor stream for (a).

17. The process of claim 16 wherein the $CCl_3CH_2CH_2Cl$ is reacted in a reactor which is free of added catalyst.

18. The process of claim 15 wherein $CCl_3CH_2CHCl_2$ is reacted with HF to form $CF_3CH=CHCl$, and the fluorination product comprising $CF_3CH=CHCl$ is used as the precursor stream for (a).

19. The process of claim 15 wherein $CCl_3CH_2CCl_3$ is reacted with HF to form $CF_3CH=CCl_2$ and $CF3CH_2CCl_2F$ and the fluorination product comprising $CF_3CH=CCl_2$ and $CF_3CH_2CCl_2F$ is used as the precursor stream for (a).

20. The process of claim 15 wherein $CF_3CCl_2CF_3$ is produced in (a), and $CF_3CH_2CF_3$ is produced in (c).

* * * * *